US005089046A

United States Patent [19]
Lee et al.

[11] Patent Number: 5,089,046
[45] Date of Patent: Feb. 18, 1992

[54] ARYL AND HETEROARYL DIONES

[75] Inventors: Shy-Fuh Lee, Sunnyvale; Richard J. Anderson, Palo Alto; Gary W. Luehr, Sacramento; G. Wayne Craig, Mountain View, all of Calif.; Joel L. Kirkpatrick, Barrington, Ill.; Takashi Nishizaka; Kenichi Komatsubara, both of Kawasaki, Japan

[73] Assignee: Sandoz Ltd., Basel, Switzerland

[21] Appl. No.: 416,173

[22] Filed: Oct. 2, 1989

Related U.S. Application Data

[63] Continuation-in-part of Ser. No. 177,192, Apr. 4, 1988, abandoned.

[51] Int. Cl.⁵ .................... A01N 41/04; A01N 41/06; C07C 303/65; C07C 311/08
[52] U.S. Cl. ......................................... 71/103; 71/87; 71/86; 558/53; 558/54; 558/57; 558/412; 558/45; 558/46; 558/47; 558/190; 558/192; 558/193; 558/196; 560/12; 562/11; 562/430; 564/97; 564/99; 564/92; 564/85; 564/86

[58] Field of Search .................. 558/57, 54, 53, 412, 558/45, 46, 47, 190, 192, 193, 196; 71/103, 87, 86; 564/97, 99, 92, 85, 86; 562/430, 11; 560/12

[56] References Cited

U.S. PATENT DOCUMENTS

| 4,728,745 | 3/1988 | Carter et al. ..................... 549/417 |
| 4,780,127 | 10/1988 | Michaely et al. .................... 71/103 |
| 4,921,526 | 5/1990 | Lee et al. .................... 71/86 |

FOREIGN PATENT DOCUMENTS

| 135191 | 3/1985 | European Pat. Off. . |
| 186118 | 7/1986 | European Pat. Off. . |
| 186119 | 7/1986 | European Pat. Off. . |
| 186120 | 7/1986 | European Pat. Off. . |
| 255584 | 2/1988 | European Pat. Off. . |

Primary Examiner—Nicky Chan
Attorney, Agent, or Firm—Allen E. Norris

[57] ABSTRACT

Cyclic 1-one-2-ene-3-ol compounds substituted in 2-position by an aroyl or heteroaroyl group bearing a hydrocarbylsulfonyloxy or hydrocarbylsulfonylamino substituent exhibiting herbicidal activity.

14 Claims, No Drawings

ARYL AND HETEROARYL DIONES

This is a continuation-in-part of Ser. No. 177,192 filed on Apr. 4, 1988, now abandoned.

This invention relates to novel substituted aryl or heteroaryl diones and related compounds, intermediates therefor, synthesis thereof, and the use of said compounds for the control of weeds and acari.

Cyclic 1-one-2-ene-3-ol compounds substituted in the 2-position by an aroyl or heteroaroyl group and enol ethers and enol esters thereof are known as herbicidal compounds. It has been found that 2-aroyl and 2-heteroaroyl-(cyclic 1-one-2-ene-3-ol) compounds, wherein the aroyl or heteroaroyl group bears a hydrocarbylsulfonyloxy and/or a hydrocarbylsulfonylamino substituent, as well as enol ethers and enol esters thereof have interesting biological properties. They are useful in agriculture, in particular for the control of undesired vegetation.

More particularly, this invention concerns compounds of the general formula

wherein

A is a cyclic 1-one-2-ene-3-ol-2yl residue;

B is an aryl or heteroaryl group bearing at least one hydrocarbyl substituent attached via an $-OSO_2-$ or $-NSO_2-$ bridge and optionally bearing further substituents; and salts, enolethers, and enolesters thereof.

The term hydrocarbyl as used herein stands for unsubstituted or substituted hydrocarbyl. The hydrocarbyl group conveniently contains from one to eight carbon atoms and may be straight or branched, saturated or unsaturated, comprise or consist of a ring which may be saturated, unsaturated or aromatic. Examples of suitable hydrocarbyl substituents are apparent from the definition $R_{12}$ hereinafter.

A particular group of compounds is that represented by formula I

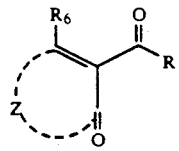

wherein

Z is a $C_2$–$C_{10}$ alkylene group, optionally substituted with one or more members selected from $C_{1-8}$alkyl, $C_{1-8}$alkoxy, $C_{1-8}$alkylthio, $COOR_{16}$, hydroxy, halogen; cyano; halogen; cyano; nitro; phenyl; $R_9SO_{n'}$; benzyl; $-NR_{10}R_{11}$; $R_{12}C(O)-$; $-SO_2NR_{10}R_{11}$; and $-N(R_{10})C(O)R_{11}$; said Z group further being optionally interposed by one or two members selected from an oxygen atom, a group $-S(O)_p-$, a group

a group $-N(R_{18})-$ or a carbonyl group; and whereby two of any alkyl substitutents may be joined to form a bicyclic, spiro or bridged ring;

R is phenyl or a 5- or 6-membered aromatic heterocycle containing one or two heteroatoms selected from oxygen, sulfur, and nitrogen; R being substituted by at least one member selected from the group consisting of $-OSOR_2R_{12}$ and $-NR_{15}SO_2R_{12}$; R being optionally further substituted by one or two members selected from $C_{1-8}$alkyl, optionally substituted with one to six halogen atoms; $C_{1-8}$alkoxy, optionally substituted with one to six halogen atoms; $C_{1-8}$alkylcarbonyl, $C_{1-8}$alkoxycarbonyl; phenyl; halogen; cyano; nitro; $-(O)_{n}$-$S(O)_{n'}R_9$; $NR_{10}R_{11'}$; $-SO_2NR_{10}R_{11'}$; $-N(R_{10'})$-$C(O)R_{11'}$; or $-NR_{15'}SO_2R_{12'}$; whereby any two adjacent alkyl substituents may be joined to form a bicyclic alkylene ring;

$R_6$ is hydrogen; $C_{1-8}$alkyl; optionally substituted $C_{1-8}$alkylcarbonyl; optionally substituted $C_{1-8}$alkoxycarbonyl; $C_{1-8}$alkylsulfonyl; $C(O)NR_{13}R_{14}$; $P(O)(OR_{11})_2$; $R_{13}P(O)OR_{11}$ optionally substituted benzoyl; or a salt forming moiety.

$R_9$ and $R_{9'}$ are independently phenyl; benzyl; or $C_{1-8}$alkyl, optionally substituted by one or more members selected from halogen, cyano, $C_{1-2}$alkoxy or $C_{1-2}$alkylthio;

$R_{10}$, $R_{10'}$, $R_{11}$, $R_{11'}$, $R_{11''}$, $R_{13}$, $R_{14}$, $R_{15}$, $R_{15'}$ and $R_{16}$ are independently hydrogen or $C_{1-8}$alkyl;

$R_{12}$ and $R_{12'}$are independently $C_{1-8}$alkyl, optionally substituted with one to six halogen atoms; or phenyl optionally substituted with one to three members selected from $C_{1-8}$alkyl, $C_{1-8}$alkylcarbonyl, $C_{1-8}$alkoxycarbonyl, $C_{1-8}$alkylsulfonyl, $C(O)NR_{13}R_{14}$, $P(O)(OR_{11''})$ and $R_{13}P(O)OR_{11''}$;

$R_{17}$ is $C_{1-8}$alkyl or $C_{1-8}$alkoxy;

$R_{18}$ is hydrogen or $C_{1-8}$alkyl;

n' and p are independently 0, 1 or 2; and n and s are independently 0 or 1.

Enol compounds of the formula (I), wherein $R_8$ is H, can exist in a number of tautomeric forms, the following being representative:

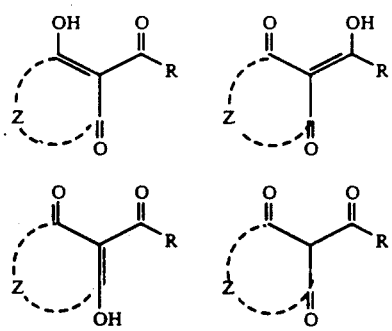

It is intended that all such tautomeric structures are included within the scope of this invention.

In preferred compounds of formula I, Z is an unsubstituted or substituted $C_{2-3}$alkylene group.

Where Z is substituted by $C_{1-8}$alkyl, it is preferably substituted by $C_{1-4}$alkyl.

Where Z is substituted by $C_{1-8}$alkoxy, it is preferably substituted by $C_{1-4}$alkoxy.

Where Z is substituted by $C_{1-8}$alkylthio, it is preferably substituted by $C_{1-4}$alkylthio.

Where Z is substituted by halogen, it is preferably bromo, chloro, or fluoro.

Where any two alkyl substituents of Z are joined to form a bicyclic, spiro or bridged alkylene ring, such alkylene ring preferably has one to five carbons.

Preferred substitutents of Z are $C_{1-4}$alkyl, $SC_{1-4}$alkyl, and $SO_2C_{1-4}$alkyl.

Where Z is interposed, it is preferably interposed by an oxygen or sulfur atom, a $N(R_{18})$ group or a carbonyl group or both of the latter.

Where R is an aromatic heterocycle, it is, e.g., a thienyl, pyrazolyl, pyridyl or pyrimidinyl, preferably a pyrimidinyl ring.

R is preferably substituted phenyl.

Where R is further substituted, it is preferably further substituted by one or two substituents, those substituents being selected from $C_{1-4}$alkyl, $C_{1-4}$alkoxy, $NO_2$, bromo, chloro and fluro.

Where any two alkyl substituents of R are joined to form a bicyclic ring, such alkylene ring preferably has three to four carbon atoms.

Where any of $R_8$, $R_9$, $R_{9'}$, $R_{10}$, $R_{10'}$, $R_{11}$, $R_{11'}$, $R_{11''}$, $R_{13}$, $R_{14}$, $R_{15}$, $R_{15'}$, $R_{16}$, $R_{12}$, $R_{12'}$, $R_{17}$ and $R_{18}$ is or contains alkyl, it is preferably $C_{1-4}$alkyl.

Where any of $R_8$, $R_{12}$, $R_{12'}$, $R_{13}$, $R_{17}$ is or contains alkoxy, it is preferably $C_{1-8}$alkoxy.

$C_{1-8}$alkoxycarbonyl and $C_{1-8}$alkylcarbonyl contain a $C_{1-8}$alkoxy or a $C_{1-8}$alkyl group attached to a carbonyl.

Examples of various preferred compound groups comprising $R_8$ are a) $R_8$=hydrogen, $C_{1-8}$alkyl, $C_{1-8}$alkylcarbonyl, $C_{1-8}$alkoxycarbonyl, $C(O)NR_{13}R_{14}$, $C_{1-8}$alkylsulfonyl, $P(O)-(OR_{11})_2$, $R_{13}P(O)OR_{11}$ or benzoyl or a salt forming moiety b) $R_8$=hydrogen, $C_{1-4}$alkyl, $C_{4-8}$alkylcarbonyl, benzoyl or $C_{1-4}$alkylsulfonyl c) hydrogen, methyl, ethyl, t-butylcarbonyl, isobutylcarbonyl, benzoyl or methylsulfonyl d) hydrogen e) optionally substituted $C_{1-8}$alkylcarbonyl, optionally substituted $C_{1-8}$alkoxycarbonyl, optionally substituted benzoyl f) $C_{1-8}$alkoxycarbonyl.

Where $R_8$ is a salt forming moiety, it may be inorganic e.g. a metal equivalent of Na, Ca, Fe or Cu; or organic, e.g., the ammonium salt moiety of an amine e.g. 1-(methylaminoethyl)naphthalene), a sulfonium, sulfoxomium or phosphonium moiety. Preferred examples of ammonium salts are those derived from amines having the formula X.

$$\begin{array}{c} R_{21} \\ | \\ N-R_{22} \\ | \\ R_{23} \end{array} \quad (X)$$

wherein each of $R_{21}$, $R_{22}$ and $R_{23}$ represents independently hydrogen, $C_{1-16}$alkyl optionally substituted by one or more hydroxy groups, $C_{2-4}$alkenyl or $R_{21}$ and $R_{22}$ form together a $C_{2-5}$alkylene group which may optionally be interrupted by oxygen. Depending on the nature of $R_8$, the salt may exist in chelated form.

$R_{12}$ is preferably phenyl or $C_{1-4}$alkyl, optionally substituted with one to three halogen atoms; more preferably phenyl or $C_{1-3}$alkyl, optionally substituted with one to three bromo, chloro, or fluoro atoms.

$R_{15}$ is preferably hydrogen or $C_{1-4}$alkyl, more preferably hydrogen. Combinations of these preferences are particularly preferred.

A particular subgroup of compounds of formula I is that represented by formula Ia

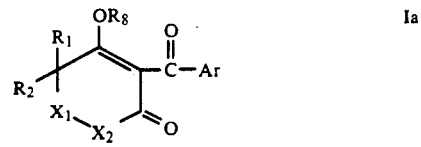

wherein
Ar is selected from the groups

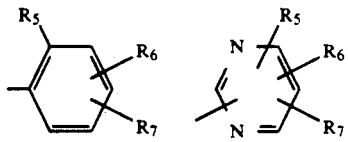

one of $X_1$, $X_2$ represents oxygen, $S(O)_{n'}$, $CR_{1'}R_{2'}$ or $NR_{18}$ and the other represents

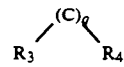

$R_1$, $R_{1'}$, $R_2$, $R_{2'}$, $R_3$ and $R_4$ are independently hydrogen, $C_{1-8}$alkyl, $C_{1-8}$alkoxy, $C_{1-8}$alkylthio or $COOR_{16}$ and $R_4$ may additionally represent hydroxy or $R_1$ and $R_2$ together form a $C_{3-6}$alkylene, or $R_2$ and $R_{2'}$ when on adjacent carbon atoms together form an additional bond or a $C_{1-4}$alkylene bridge optionally substituted with one to six $C_{1-8}$alkyl or groups or $R_3$ and $R_4$ together form a $C_{3-6}$alkylene or together with the carbon to which they are attached form a carbonyl group.

$R_5$ is $C_{1-8}$alkyl, optionally substituted with one to six halogen atoms; $C_{1-8}$alkoxy, optionally substituted with one to six halogen atoms; $-(O)_nS(O)_{n'}R_{12}$; $-NR_{15}SO_2R_{12}$; halogen; cyano; or nitro;

each of $R_6$ and $R_7$ is independently hydrogen or selected from the values of $R_5$; with the proviso that at least one of $R_5$, $R_6$ and $R_7$ is a group $-OSO_2R_{12}$ or $-NR_{15}SO_2R_{12}$;

$R_8$, $R_{12}$, $R_{15}$, $R_{16}$, n and n' are as previously defined; and q is 0 or 1.

A particularly subgroup of compounds Ia (compounds Iaa) is that wherein
$X_1$ is oxygen, $S(O)_{n'}$, $CR_{1'}R_{2'}$ or $NR_{18}$,
$X_2$ is

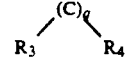

each of $R_1$, $R_{1'}$, $R_2$, $R_{2'}$, $R_3$ and $R_4$ is independently hydrogen, $C_{1-8}$-alkyl or $COOR_{16}$, or $R_1$ and $R_2$ together form a $C_{3-6}$alkylene; or $R_2$ and $R_{2'}$ together form a $C_{1-4}$alkylene optionally substituted with 1 to 6 $C_{1-8}$alkyl groups;

$R_5$ is $C_{1-8}$alkyl, optionally substituted with one to six halogen atoms; $C_{1-8}$alkoxy, optionally substituted with one to six halogen atoms; $O_nS(O)_{n'}R_{12}$; halogen; cyano; or nitro;

each of $R_6$ and $R_7$ is independently hydrogen or selected from the values of $R_5$; with the proviso that at least one of $R_5$, $R_6$ and $R_7$ is the group $OSO_2R_{12}$; or $NR_{15}SO_2R_{12}$;

$R_8$, $R_{12}$, $R_{15}$, $R_{16}$, $R_{18}$, n and n' are as previously defined; and q is 0 or 1.

A particular sub-group of compounds Ia (Compounds Iaa) is that wherein $X_1$ is oxygen, $S(O)_{n'}$, $CR_1'R_2'$ or $NR_{18}$,
$X_2$ is

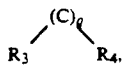

each of $R_1$, $R_{1'}$, $R_2$, $R_{2'}$, $R_3$ and $R_4$ is independently hydrogen, $C_{1-8}$alkyl or $COOR_{16}$, or $R_1$ and $R_2$ together form a $C_{3-6}$alkylene; or $R_2$ and $R_{2'}$together form a $C_{1-4}$alkylene optionally substituted with 1 to 6 $C_{1-8}$alkyl groups;

$R_5$ is $C_{1-8}$alkyl, optionally substituted with one to six halogen atoms; $C_{1-8}$alkoxy, optionally substituted with one to six halogen atoms; $O_nS(O)_{n'}R_{12}$; $NR_{15}SO_2R_{12}$; halogen; cyano; or nitro;

each of $R_6$ and $R_7$ is independently hydrogen or selected from the values of $R_5$; with the proviso that at least one of $R_5$, $R_6$ or $R_7$ is the group $OSO_2R_{12}$; or $NR_{15}SO_2R_{12}$;

$R_8$ is hydrogen, $C_{1-8}$alkyl, $C_{1-8}$alkylcarbonyl, $C_{1-8}$alkoxycarbonyl, $C(O)NR_{13}R_{14}$, ($C_{1-8}$alkyl)sulfonyl, $P(O)-(OR_{11})_2$ or $R_{13}P(O)OR_{11}$;

$R_{18}$ is $C_{1-8}$alkyl;

$R_{12}$ is $C_{1-8}$alkyl, optionally substituted with one to six halogen atoms;

each of $R_{13}$, $R_{14}$, $R_{15}$ and $R_{16}$ is, independently, hydrogen, or $C_{1-8}$alkyl;

n is zero or one n' is zero, one or two; and q is zero or one.

A further subgroup of compounds Ia (compounds Iab) is that wherein $X_1$ is oxygen, $S(O)_{n'}$, $CR_1'R_2'$ or $NR_{18}$
$X_2$ is

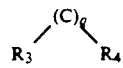

$R_1$, $R_{1'}$, $R_2$, $R_{2'}$, $R_3$ and $R_4$ are independently hydrogen, $C_{1-8}$alkyl, $C_{1-8}$alkoxy, $C_{1-8}$alkylthio, or $COOR_{16}$; or $R_1$ and $R_2$ together form a $C_{3-6}$alkylene; or $R_2$ and $R_{2'}$together form a $C_{2-4}$alkylene optionally substituted with one to six $C_{1-8}$alkyl groups; or $R_3$ and $R_4$ together form a $C_{3-6}$alkylene;

$R_5$ is $C_{1-8}$alkyl, optionally substituted with one to six halogen atoms; $C_{1-8}$alkoxy, optionally substituted with one to six halogen atoms; $-(O)_nS(O)_{n'}R_{12}$; $-NR_{15}SO_2R_{12}$; halogen; cyano; or nitro;

each of $R_6$ and $R_7$ is independently hydrogen or selected from the values of $R_5$; with the proviso that at least one of $R_5$, $R_6$ and $R_7$ is a group $-OSO_2R_{12}$ or $-NR_{15}SO_2R_{12}$;

$R_6$ is hydrogen, $C_{1-8}$alkyl; $C_{1-8}$alkylcarbonyl; $C_{1-8}$alkoxycarbonyl; $C_{1-8}$alkylsulfonyl; $C(O)NR_{13}R_{14}$; $P(O)(OR_{11})_2$; $R_{13}P(O)OR_{11}$; or a salt forming moiety.

$R_{12}$, $R_{15}$, $R_{16}$, n, and n' are as previously defined; and q is 0 or 1. In preferred compounds of formula Ia particular meanings of $X_1$ and $X_2$ are as follows a)
i) $X_1 = O$, S, $CR_1'R_2'$; $X_2 = CR_3R_4$ ii) $X_1 = CR_1'R_2'$; $X_2 = CR_3R_4$ (other than as C=O)

b)
i) $X_1 = CR_3R_4$; $X_2 = NR_{18}$ ii) $X_1 = C=O$; $X_2 = NR_{18}$ iii) $X_1 = =C-$ (with $R_1$); $X_2 = NR_{18}$
$\quad\quad\quad |$
$\quad\quad\quad R_3$ c)
i) $X_1 = C=O$; $X_2 =$ oxygen, $S(O)_{n'}$ or $CR_1'R_2'$ ii) $X_1 = C=O$; $X_2 = CR_1'R_2'$ Ar is preferably substituted phenyl.

Where any of the substituents $R_5-R_7$ and $R_{12}$ is or contains halogen, such halogen is preferably selected from bromo, chloro and fluoro.

Where any of $R_1$, $R_{1'}$, $R_2$, $R_{2'}$, $R_3$, $R_4$, $R_5$, $R_6$, $R_7$, $R_8$, $R_{12}-R_{16}$, and $R_{18}$ is or contains alkyl, it is preferably of one to four carbons.

Where $R_1$ and $R_2$, $R_2$ and $R_{2'}$, or $R_3$ and $R_4$ together form an alkylene, it is preferably of two to five carbon atoms.

Where any of $R_5-R_8$ are or contains $C_{1-8}$alkoxy, it is preferably of one to four carbons.

Each of $R_1$, $R_{1'}$, $R_2$, $R_{2'}$, $R_3$ and $R_4$ individually is preferably hydrogen or $C_{1-4}$alkyl; such alkyl is more preferably of one to three carbons.

$R_5$ is preferably $-(O)_nS(O)_{n'}C_{1-4}$alkyl, halogen, nitro or $C_{1-4}$alkyl optionally substituted with halogen, more preferably methyl, $CF_3$, $C_{1-3}$alkylsulfonyl, $C_{1-3}$alkylsulfonyloxy, chloro, bromo or nitro, still more preferably nitro.

$R_6$ is preferably hydrogen, $C_{1-4}$alkyl, $C_{1-4}$alkoxy, $C_{1-3}$alkylsulonyloxy, bromo or chloro. $R_6$ is more preferably hydrogen, methoxy, methylsulfonyloxy or chloro, still more preferably hydrogen.

$R_7$ is preferably bromo chloro, $OSO_2C_{1-4}$alkyl, $OSO_2C_{1-4}$haloalkyl, $OSO_2$phenyl or $NR_{15}SO_2C_{1-4}$alkyl. $R_7$ is more preferably chloro, $OSO_2$phenyl or $C_{1-3}$alkylsulonyloxy, still more preferably $C_{1-2}$alkylsulfonyloxy.

$R_8$ has the preferences described above in connection with formula I.

$R_{12}$ is preferably phenyl or $C_{1-4}$alkyl, optionally substituted with one to three halogen atoms; more preferably phenyl or $C_{1-3}$alkyl, optionally substituted with one to three bromo, chloro or fluoro atoms.

$R_{15}$ is preferably H or $C_{1-4}$alkyl, more preferably H.

$R_{18}$ is preferably hydrogen or $C_{1-4}$alkyl.

q is preferably 1.

n' is preferably 0 or 2.

Preferably $R_6$ is in the 3-position and $R_7$ is in the 4-position.

In the description and claims hereinafter, each of $R-R_{18}$, $R_{21}-R_{23}$, X, Z, n, n', q, p and s is as defined above, unless otherwise specified.

The compounds of the present invention of formula I are new substances which can be prepared by methods analogous to methods known in the art for the preparation of 2-aroyl-(cyclic-1,3-diones) and enol ethers or enol esters thereof.

More particularly, they can be obtained by, for example: reacting an enol ester of formula (II)

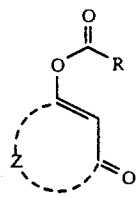
(II)

wherein R and Z are as defined above with a cyanide source and a moderate base to give a compound of formula I where $R_8$ is hydrogen, followed, where desired, by etherification or esterification to the corresponding enol ethers or enol esters.

Similarly the compounds of formula Ia can be obtained by, for example: reacting an enol ester of formula (IIa)

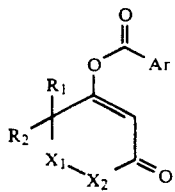
(IIa)

wherein Ar, $X_1$, $X_2$, $R_1$ and $R_2$ are as defined above, with a cyanide source and a moderate base to obtain a compound of formula Ia where $R_8$ is hydrogen, followed, where desired, by etherification or esterification to the corresponding enol ethers or enol esters.

The above reaction is carried out in the presence of a catalytic amount of a source of cyanide anion and/or hydrogen cyanide, together with a molar excess, with respect to the enol ester, of a moderate base. The reaction is conveniently carried out in a solvent which is inert under the reaction conditions, e.g. 1,2-dichloroethane, toluene, acetonitrile, methylene chloride, ethyl acetate, dimethylformamide (DMF) and methyl isobutyl ketone (MIBK). In general depending on the nature of the reactants and the cyanide source, the rearrangement can be conducted at temperatures up to about 80° C. In some cases, for instance when there is a possible problem of excessive by-product formation, the temperatures should be kept at about 40° C. maximum.

Preferred cyanide sources are alkali metal cyanides such as sodium and potassium cyanide; cyanohydrins of methyl alkyl ketones having from 1-4 carbon atoms in the alkyl groups, such as acetone or methyl isobutyl ketone cyanohydrins; cyanohydrins of benzaldehyde or of $C_2$-$C_5$ aliphatic aldehydes such as acetaldehyde, propionaldehyde, etc., cyanohydrins; zinc cyanide; tri(-lower alkyl) silyl cyanides, notably trimethyl silyl cyanide; and hydrogen cyanide itself. Among cyanohydrins the preferred cyanide source is acetone cyanohydrin. The cyanide source is used in an amount up to about 50 mole percent based on the enol ester. Generally about 1-10 mole % of the cyanide source is preferred.

By the term "moderate base" is meant a substance which acts as a base yet whose strength of activity as a base lies between that of strong bases such as hydroxides (which could cause hydrolysis of the enol ester) and that of weak bases such as bicarbonates (which would not function effectively). Moderate bases suitable for use in this reaction include both organic bases such as tertiary amines and inorganic bases such as alkali metal carbonates and phosphates. Suitable tertiary amines include trialkylamines such as triethylamine, trialkanolamines such as triethanolamine, and pyridine. Suitable inorganic bases include potassium carbonate and trisodium phosphate. The base is used in an amount of from about 1 to about 4 moles per mole of enol ester, preferably about 1.3-2 moles per mole.

When the cyanide source is an alkali metal cyanide, particularly potassium cyanide, a phase transfer catalyst may be included in the reaction. Particularly suitable phase transfer catalysts are the Crown ethers.

Depending on the reaction conditions, the thus obtained keto-enol compounds may be in free acid form ($R_8$ is H) or in salt form; where they are in salt form (i.e. $R_8$ is a salt forming moiety), $R_8$ may be inorganic (e.g. a metal equivalent of Na, Ca, Fe or Cu) or organic, e.g. the ammonium salt moiety of an amine, sulfonium, sulfoxonium or phosphonium moiety. Depending on the nature of $R_8$, the salt may exist in chelated form. The salt form may be converted to the corresponding acid form ($R_8$ is H) in a manner known per se, and vice versa.

Compounds of formula I where $R_8$ is other than hydrogen or salt forming moiety can be prepared in a manner known per se for the preparation of enol ethers or enol esters form the corresponding enol compounds, e.g. by reacting a compound of formula I where $R_8$=H with either a) the group $R_8$—OH and a catalyst, or
b) the group $R_8$—Q and a moderate base, wherein Q is a halogen atom, to give a compound of formula I where $R_8$ is as defined above other than hydrogen or a salt forming moiety.

The above reaction a) is carried out in the presence of a catalyst such as concentrated sulfuric acid. The reaction is conveniently carried out in a solvent which is also the reactant such as methanol, and at an elevated temperature.

The above reaction b) is carried out in the presence of a moderate base such as triethylamine or pyridine and conveniently at RT or below.

The compounds of formula I may be recovered from the reaction mixture in which they are formed by working up by established procedures.

The starting materials and reagents employed in the process described herein are either known or, insofar as they are not known, may be produced in a manner analogous to the processes described herein or to known processes.

The novel compounds of formula I are useful for the control of weeds, using pre- and/or post-emergent treatments. Compounds of formula I are also useful as plant growth regulators and as acaricides. The compounds can be applied for example in the form of dusts, granules, solutions, emulsions, wettable powders, flowables and suspensions. Application of a compound of the present invention as a herbicide is made according to conventional procedure to the weeds or their locus using one-half or less to ten pounds or especially one-tenth or less (e g. one-fiftieth) to ten pounds per acre (ca 0.56 to 11.2 especially 0.112 to 11.2 kg/ha). Application as a selective herbicide in rice is made for example at a rate of ca 5 to 1000 g preferably 10 to 500 g especially 20 to 200 g per hectare. The application of a compound of the present invention to the "locus" of the weed included application to the seeds, the plant (weed) or parts of the plant or the soil.

The term "herbicide," as used herein, refers to an active ingredient which modifies the growth of plants because of phytotoxic or plant growth regulating properties so as to retard the growth of the plant or damage the plant sufficiently to kill it.

The compounds of the present invention, when applied as either post or pre-emergents, demonstrate high levels of herbicidal activity on broadleaf, grass and sedge weeds.

Thus the compounds are useful in combatting weeds in corn and wheat without damaging crop cultures. Both grassy and broadleaf weeds are controlled with control of the latter being particularly good.

Compounds of the invention exhibit selectivity in various crops. Additionally certain compounds of formula I such as those wherein $R^8$ is hydrogen or especially has the meanings given above under e) and f) or is an ammonium salt derived from an amine of formula X as defined above exhibit acceptable rice tolerance with excellent weed control and are thus useful for combatting weeds in rice especially in transplanted (paddy) rice.

Compounds of this type wherein

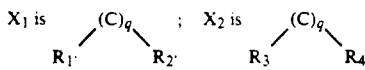

and Ar is o-nitro-p-$(O_nS(O)_n\cdot R_{12})$ phenyl are especially preferred for this use. Examples of weeds which may be selectively combatted by both pre- and post-emergent application in rice include Echinochloa spp e.g. barnyard grass, Cyperus spp e.g. flatsedge, bullrush, spikerush, water nutsedge, Rumex spp, Sagitaria spp e.g. arrowhead, Monochoria spp and Serbania spp. They have an excellent herbicidal activity on weeds prior to germination and during growth and are useful as herbicides for soil treatments before and after transplantation of young rice plants, during the growth of crops and for culm and foliage treatments before transplantation and during the growth of crops. The invention also provides herbicidal compositions suitable for use in rice locus.

In the use of the compounds of formula I as a herbicide or acaricide, a compound of formula I, or mixtures thereof, can conveniently be employed as agricultural compositions in association with acceptable diluent(s) for application to the weed, aracri, or their loci. Such compositions also form part of the present invention.

Methods of preparing suitable compositions which can be used with a compound of the present invention are described in the literature along with suitable liquid and solid carriers, such as in U.S. Pat. No. 4,192,669 and 4,163,661, which are incorporated herein by reference. The optimum usage of a compound of the present invention will depend on various factors such as weed to be treated, incidence and/or growth of weeds, weather, environmental conditions, formulation, application method, locus, timing and the like and is readily determinable by one of ordinary skill in the art using routine testing such as greenhouse testing and small plot testing.

The compounds of the present invention can be compounded with appropriate inert carriers, if necessary, and additivies in an appropriate ratio by means of dissolving, separating, suspending, mixing, impregnating, adsorbing or precipitating operation to formulate into dusts, suspensions, suspension concentrates, emulsions, solutions, wettable powders, flowables, granules or tablets.

A wide variety of solids and liquids can be used as the inert diluents or carriers in the present invention. Examples of materials which can be used as the solid carriers include vegetable powders such as soybean meal, corn meal, wood meal, bark meal, sawdust, tobacco stem meal, walnut shell flour, bamboo meal, fibrous meal and residue after the extraction of vegetable extract; synthetic polymers such as crushed synthetic resins; inorganic mineral powders such as clay (e.g., kaolin, bentonite, terra abla), talc (e.g. talc, pyrophylite), silica (e.g. diatomaceous earth, siliceous sand, mica, white carbon [synthetic colloidal silica called hydrated fine silicon powder, hydrated silicic acid, or a product mainly composed of calcium silicate], activated carbon, sulfur powder, pumice stone, calcined diatomaceous earth, crushed brick, fly ash, sand, calcium carbonate and calcium phosphate; and chemical fertilizers such as ammonium sulfate, ammonium phosphate and ammonium nitrate and compost. These diluents or carriers may be used either alone or in a combination of two or more of them. As the liquid carriers, there can be used materials which themselves have an ability as solvent as well as materials which themselves do not have an ability as solvent, but can disperse active ingredients by the aid of other additives. Examples of the materials which can be used as the liquid carriers include water, alcohols (e.g., methanol, ethanol, isopropanol, butanol, ethylene glycol), ketones (e.g.. acetone, methyl ethyl ketone, methyl sobutyl ketone, diisobutyl ketone, cyclohexanone), ethers (e.g., ethyl ether, dioxane, cellosolve, dipropyl ether, tetrahydrofuran), aliphatic hydrocarbons (e.g., gasoline, diesel oil, mineral oil), aromatic hydrocarbons (e.g., benzene, toluene, xylene, solvent naphtha, alkylnaphthalenes), halogenated hydrocarbons (e.g., dichloroethane, chlorinated benzene, chloroform, carbon tetrachloride), esters (e.g., ethyl acetate, dibutyl phthalate, diisopropyl phthalate, dioctyl phthalate), acid amides (e.g., dimethylformamide, diethylformamide, dimethylaceamide), nitriles (e.g., acetonitrile) and dimethyl sulfoxide. These liquid carriers may be used either alone or as a mixture of two or more of them.

In some cases, other additives are used either alone or as a mixture of two or more In some cases, no additive is used. Surfactants are used for the purposes of emulsifying, dispersing, spreading, solubilizing and/or wetting the compounds as active ingredients. Examples of the surfactants include polyoxyethylene alkylaryl ethers, polyoxyethylene alkyl ethers, polyoxyethylene higher fatty acid esters, lauryl sulfate, polyoxyethylene resin acid esters, polyoxyethylene sorbitan monolaurate, polyoxyethylene sorbitan monoleate, alkylarylsulfonates, naphthalenesulfonic acid condensate, lignosulfonates and higher alcohol sulfuric esters. For the purposes of dispersion-stabilizing, tackifying and bonding the compound of the active ingredients, there can be used, for example, casein, gelatin, starch, alginic acid, methyl cellulose, carboxymethyl cellulose, gum arabic, polyvinyl alcohol, pine oil, tung oil, bentonite and lignosulfonates.

For the purpose of improving the fluidity of solid products, there may be used wax, stearates and alkyl phosphates.

Naphthalenesulfonate condensates and condensed phosphates may be used as peptizers for suspension products.

If desired, anti-foaming agents such as silicone oil, anti-caking agents or anti-corrosion agents may be added.

Alternatively, the compounds of formula I may be used in microencapsulated form.

The compounds of formula I can be combined with a cyclodextrin to make a cyclodextrin inclusion complex for application to the pest or weed or its locus.

Suitable formulations contain from 0.01 to 99% by weight of active ingredient, from 0 to 20% of surfactant and from 1 to 99.99% of solid or liquid diluent(s). Higher ratios of surfactant to active ingredient are sometimes desirable and are achieved by incorporation into the formulation or by tank mixing. Application forms of a composition generally contain between 0.01 and 25% by weight of active ingredient. For example powders or granules may in general contains 0.2 to 20% by weight of active ingredient. Emulsions or wettable formulations will generally contain 0.1 to 50% by weight of active ingredients. Lower or higher levels of active ingredient can, of course, be present depending on the intended use, the physical properties of the compound and the mode of application. Concentrate forms of a composition intended to be diluted before use generally contain between 2 and 90%, preferably between 5 and 81% by weight of active ingredient.

EXAMPLE A

Preparation of a Dust

10 Parts of a compound according to this invention and 90 parts of powdered talc are mixed in a mechanical grinder-blender and are ground until a homogeneous, free-flowing dust of the desired particle size is obtained. This dust is suitable for direct application to the site of the weed, acari infestation.

EXAMPLE B

Preparation of a Wettable Powder

25 Parts of a compound according to this invention are mixed and milled with 25 parts of synthetic fine silica, 2 parts of sodium lauryl sulphate, 3 parts of sodium ligninsulphonate and 45 parts of finely divided kaolin until the mean particle size is about 5 micron. The resulting wettable powder is diluted with water before use to a spray liquor with the desired concentration.

EXAMPLE C

Preparation of Emulsifiable Concentrate (EC)

13.37 Parts of a compound according to this invention are mixed in a beaker with 7.04 parts of Toximul 360A (a mixture of anionic and non. ionic surfactants containing largely anionic surfactants), 23.79 parts of dimethylformamide and 55.8 parts of Tenneco 500-100 (predominantly a mixture of alkylated aromatics such as xylene and ethylbenzene) until solution is effected. The resulting EC is diluted with water for use.

EXAMPLE D

Wettable Powder 50 parts of the compound No. 104, 20 parts of diatomaceous earth, 22 parts of clay, 3 parts of white carbon, 2 parts of sodium lignosulfonate and 3 parts of sodium alkylnaphthalenesulfonate were mixed and crushed to obtain a wettable powder containing 50% of the active ingredient.

EXAMPLE E

Granule 0.35 parts of the compound No. 105, 25 parts of bentonite, 70.65 parts of talc, 2 parts of sodium dodecylbenzenesulfonate and 2 parts of sodium lignosulfonate were mixed. About 20 parts of water was added thereto. The mixture was kneaded in a kneader, granulated in a granulator and dried. Dressing of grain was conducted to obtain a granule containing 0.35% of the active ingredient.

The compositions of this invention can also comprise other compounds having biological activity, e.g. compounds having similar or complementary herbicidal activity for broadspectrum weed control or compounds having acaricidal activity or compounds having antidotal, fungicidal, insecticidal or insect attractant activity.

The following examples are provided to illustrate the practice of the present invention. Temperature is given in degrees Centigrade. RT means room temperature. Parts and percentages are by weight.

PREPARATION OF FINAL COMPOUNDS

EXAMPLE 1

To a solution of 2,2,6,6-tetramethyl-5-(3-methoxy-4-methylsulfonyloxy-2-nitrobenzoyloxy)-3,6-dihydro-2H-pyran-3-one (7 80 g) in 50 ml of acetonitrile are added triethylamine (4.91 ml, 2 eq.) and acetone cyanohydrin (1.0 ml) in one portion. The mixture is stirred at RT overnight, after which it is diluted with water and extracted with ether. The ether is removed and the residue is purified by PTLC to give 2,2,6,6-tetramethyl-4-(3-methoxy-4-methylsulfonyloxy-2-nitrobenzoyl)-2H-pyran3,5-(4H,6H)-dione (compound 1, Table A).

EXAMPLE 2

To a solution of 5-methyl-1-(4-methylsulfonyloxy-2-chlorobenzoyloxy)-1-cyclohexane-3-one (5.30 g) in 25 ml of acetonitrile are added triethylamine (3.97 ml, 2 eq.) and acetone cyanohydrin (0.4 ml), and the mixture is stirred at RT overnight. The acetonitrile is removed, and the residue is taken up in water and extracted with methylene chloride. The combined organic extracts are washed with dilute HCl and with brine, dried and evaporated to dryness. The crude product is crystallized from ether to give 5-methyl-2-(4-methylsulfonyloxy-2-chlorobenzoyl)-cyclohexane-1,3-dione (compound 32, Table A).

EXAMPLE 3

Following the procedures of Examples 1 and 2, each of the compounds under Table A is prepared by rearrangement of the corresponding enol ester.

EXAMPLE 4

A solution of 2,2,6,6-tetramethyl-4-(4-methylsulfonyloxy-2-nitrobenzoyl)-2H-pyran-3,5-(4H,6H -dione (2.54 mmol) and 2 drops of conc. sulfuric acid in 20 ml of methanol is heated under reflux for 48 hours. The reaction mixture is concentrated and the residue is taken up in ether. The ethereal solution is washed with aqueous sodium bicarbonate and with brine, dried and evaporated to dryness to give 2,2,6,6-tetramethyl-4-(4-methylsulfonyloxy-2-nitrobenzoyl)-5methoxy-3,6-dihydro-2H-pyran-3-one.

EXAMPLE 5

To a mixture of 2,2,6,6-tetramethyl-4-(4-methylsulfonyloxy-2-nitrobenzoyl)-2H-pyran-3,5-(4H-6H)-dione (2.26 mmol) in methylene chloride (10 ml) containing triethylamine (0.47 ml, 3.39 mmol) is added dropwise at 0° a solution of acetyl chloride (0.27 g, 3 39 mmol) in 4 ml of methylene chloride. The resulting mixture is stirred for 30 min., and is then diluted with methylene chloride, washed, dried and evaporated to dryness to give 2,2,6,6-tetramethyl-4-(4-methylsulfonyloxy-2-nitrobenzoyl)-5-acetoxy-3,6-dihydro-2H-one.

EXAMPLE 6

Following the procedure of Example 5, the final compounds under column I are prepared by the reaction of 2,2,6,6-tetramethyl-4-(4-methylsulfonyloxy-2-nitrobenzoyl)-2H-pyran-3,5-(4H,6H)-dione with the corresponding acyl chloride.

- I 100. 2,2,6,6-tetramethyl-4-(4-methylsulfonyloxy-2-nitrobenzoyl)-5-propionyloxy-3,6-dihydro-2H-pyran-3-one
101. 2,2,6,6-tetramethyl-4-(4-methylsulfonyloxy-2-nitrobenzoyl-5-isobutyryloxy-3,6-dihydro-2H-pyran-3-one
102. 2,2,6,6-tetramethyl-4-(4-methylsulfonyloxy-2-nitrobenzoyl)-5-pivaloyloxy-3,6-dihydro-2H-pyran-3-one
103. 2,2,6,6-tetramethyl-4-(4-methylsulfonyloxy-2-nitrobenzoyl)-5-benzoyloxy-3,6-dihydro-2H-pyran-3-one

EXAMPLE 7

To a solution of 2-(4-methylsulfonyloxy-2-nitrobenzoyl) cyclohexane-1.3-dione (2.0 g) and triethylamine (0.8 ml) in dichloromethane (30 ml) is added benzoyl chloride (0.77 g) in dichloromethane (5 ml) at 0°, and the mixture is stirred for an hour at 0°. The reaction mixture is diluted with dichloromethane, washed with brine, dried over anhydrous sodium sulfate and evaporated to dryness. The crude product is purified by silica gel column chromatography to give the solid which was washed with isopropyl ether.2-(4-methylsulfonyloxy-2-nitrobenzoyl)-1-benzoyloxy-1-cyclohexene-3-one (compound 104).

NMR (ppm from TMS, J:Hz, CDCl$_3$), 1.8–3.0 (m, 6H), 3.1 (s,3H), 7.2–8.0 (m, 8H).

4-(4-methylsulfonyloxy-2-nitrobenzoyl)-5-n-hexanoyloxy-3,6-dihydro-2H-pyran-3-one (compound 105) may be prepared analogously.

NMR (ppm from TMS, J:Hz, CDCl$_3$) 0.9–1.5 (m,9H), 2.1–3.0 (m,8H), 7.5 (br.s.,2H) 7.8 (br s.,1H).

EXAMPLE 8

2.33g of 4,4,6,6-tetramethyl-1-(4-methylsulfonyloxy-2-nitrobenzoyloxy)-1-cyclohexene-3,5-dione are dissolved in 30 ml acetonitrile containing 0.88 g of triethylamine and 2 drops of acetone cyanohydrin and stirred at room temperature under nitrogen atmosphere for 4 hrs. The reaction mixture is concentrated to a few mls and then partitioned between water and methylene chloride. The organic layer is then washed with 1 N HCl. The solvent is removed by evaporation after drying to give an oil which was triturated in methylene chloride to give a white precipitate which is filtered off. The filtrate is then evaporated to dryness and triturated with ether to give a white granular solid corresponding to the desired compound. 4,4,6,6-tetramethyl-2-(4-methylsulfonyloxy-2-nitrobenzoyl)cyclohexane 1,3,5-trione (Table B compound no. 70).

EXAMPLE 9

3.65 g of 4-(4-methylsulfonyloxy-2-nitrobenzoyloxy)-1,5,5-trimethyl 5,6-dihydro-2(1H)-pyridone are dissolved in 20 ml of CH$_3$CN and 2.6 ml of triethylamine and 0.26 ml of acetone cyanohydrin added. The solution is stirred overnight at RT and under N$_2$. The reaction mixture is then concentrated to ca 5 ml, diluted with 25 ml of H$_2$O and extracted with 3×15 ml of CH$_2$Cl$_2$. The combined extracts are washed with 5 ml of H$_2$, 2×10 ml of 2NHCl and 2×10 ml of saturated NaCl. The organic phase is dried over Na$_2$SO$_4$, filtered and evaporated to dryness. This residue is triturated with 50 ml of diethylether and the resulting crystalline precipitate collected, washed with 3×3 ml of diethylether and dried at RT. This procedure is repeated and the resulting crystals dissolved in 15 ml of hot ethanol. On cooling a crystalline product forms which is filtered, washed with ethanol and diethylether and dried at RT under vacuum to yield 3-(4-methylsulfonyloxy-2-nitrobenzoyl)-1,5,5-trimethyl-2,4-piperidione, m.p. 125°–127.5° (Table B, compound no. 64).

TABLE A

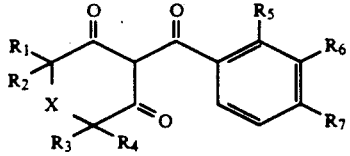

| Cpd | X | R$_1$ | R$_2$ | R$_3$ | R$_4$ | R$_5$ | R$_6$ | R$_7$ | m.p. (°C.) |
|---|---|---|---|---|---|---|---|---|---|
| 1 | O | CH$_3$ | CH$_3$ | CH$_3$ | CH$_3$ | NO$_2$ | OCH$_3$ | OSO$_2$CH$_3$ | 114 |
| 2 | O | CH$_3$ | CH$_3$ | CH$_3$ | CH$_3$ | NO$_2$ | H | OSO$_2$CH$_3$ | |
| 3 | O | CH$_3$ | CH$_3$ | CH$_3$ | CH$_3$ | Cl | H | OSO$_2$CH$_3$ | 112 |
| 4 | O | CH$_3$ | CH$_3$ | H | H | NO$_2$ | H | OSO$_2$CH$_3$ | |
| 5 | O | CH$_3$ | CH$_3$ | H | H | Cl | H | OSO$_2$CH$_3$ | |
| 6 | O | CH$_3$ | CH$_3$ | H | H | Cl | Cl | OSO$_2$CH$_3$ | |
| 7 | O | CH$_3$ | CH$_3$ | H | H | CH$_3$ | H | OSO$_2$CH$_3$ | |
| 8 | O | CH$_3$ | CH$_3$ | CH$_3$ | CH$_3$ | CH$_3$ | H | OSO$_2$CH$_3$ | |
| 9 | O | CH$_3$ | CH$_3$ | CH$_3$ | CH$_3$ | Cl | Cl | OSO$_2$CH$_3$ | |
| 10 | O | CH$_3$ | H | CH$_3$ | H | Cl | Cl | OSO$_2$CH$_3$ | |
| 11 | O | CH$_3$ | H | CH$_3$ | H | Cl | H | OSO$_2$CH$_3$ | 99 |
| 12 | O | CH$_3$ | H | CH$_3$ | H | CH$_3$ | H | OSO$_2$CH$_3$ | |
| 13 | O | CH$_3$ | H | CH$_3$ | H | NO$_2$ | H | OSO$_2$CH$_3$ | |
| 14 | O | CH$_3$ | H | CH$_3$ | H | NO$_2$ | OCH$_3$ | OSO$_2$CH$_3$ | |

TABLE A-continued

| Cpd | X | R₁ | R₂ | R₃ | R₄ | R₅ | R₆ | R₇ | m.p. (°C.) |
|-----|---|----|----|----|----|----|----|----|-----------|
| 15 | O | CH₃ | H | C₂H₅ | H | NO₂ | H | OSO₂CH₃ | 83.5-86 |
| 16 | O | CH₃ | H | C₂H₅ | H | Cl | H | OSO₂CH₃ | oil |
| 17 | O | CH₃ | H | CH₃ | H | CH₃ | H | OSO₂CH₃ | |
| 18 | O | CH₃ | CH₃ | CH₃ | CH₃ | NO₂ | H | OSO₂CH₃Cl | |
| 19 | O | CH₃ | CH₃ | CH₃ | CH₃ | Cl | H | OSO₂CH₃Cl | |
| 20 | O | CH₃ | CH₃ | CH₃ | CH₃ | CH₃ | H | OSO₂CH₃Cl | |
| 21 | O | CH₃ | H | CH₃ | H | NO₂ | H | OSO₂CH₃Cl | |
| 22 | O | CH₃ | H | CH₃ | H | Cl | H | OSO₂CH₃Cl | |
| 23 | O | CH₃ | CH₃ | CH₃ | CH₃ | OSO₂CH₃ | H | Cl | |
| 24 | O | CH₃ | CH₃ | CH₃ | CH₃ | OSO₂CH₃ | H | Br | |
| 25 | O | CH₃ | H | CH₃ | H | OSO₂CH₃ | H | Cl | |
| 26 | O | CH₃ | CH₃ | CH₃ | CH₃ | Cl | OSO₂CH₃ | Cl | |
| 27 | O | CH₃ | H | CH₃ | H | Cl | OSO₂CH₃ | Cl | |
| 28 | CH₂ | H | H | H | H | NO₂ | H | OSO₂CH₃ | 138.5-140 |
| 29 | CH₂ | H | H | H | H | Cl | H | OSO₂CH₃ | 112 |
| 30 | CH₂ | H | H | H | H | CH₃ | H | OSO₂CH₃ | |
| 31 | CH₂ | —CH₂CH₂— | H | H | NO₂ | H | OSO₂CH₃ | | |
| 32 | CH₃CH | H | H | H | H | Cl | H | OSO₂CH₃ | 107 |
| 33 | CH₃CH | H | H | H | H | NO₂ | H | OSO₂CH₃ | |
| 34 | CH₃CH | H | H | H | H | OSO₂CH₃ | H | Cl | |
| 35 | CH₃CH | H | H | H | H | Cl | H | OSO₂CF₃ | |
| 36 | CH₃CH | H | H | H | H | NO₂ | H | OSO₂CF₃ | |
| 37 | CH₃CH | H | H | H | H | NO₂ | H | NHSO₂CH₃ | |
| 38 | CH₃CH | H | H | H | H | Cl | H | NHSO₂CH₃ | |
| 39 | CH₂ | H | H | H | H | Cl | H | NHSO₂CH₃ | |
| 40 | CH₂ | H | H | H | H | NO₂ | H | NHSO₂CH₃ | |
| 41 | O | CH₃ | CH₃ | CH₃ | CH₃ | NO₂ | H | NHSO₂CH₃ | |
| 42 | O | CH₃ | CH₃ | CH₃ | CH₃ | Cl | H | NHSO₂CH₃ | |
| 43 | O | CH₃ | H | CH₃ | H | Cl | H | NHSO₂CH₃ | |
| 44 | O | CH₃ | H | CH₃ | H | NO₃ | H | NHSO₂CH₃ | |
| 45 | O | C₂H₅ | H | CH₃ | H | NO₂ | H | NHSO₂CH₃ | |
| 46 | CH₃CH | H | H | H | H | NO₂ | OCH₃ | OSO₂CH₃ | 105 |
| 47 | CH₂ | H | H | H | H | Cl | Cl | OSO₂CH₃ | 160 |
| 48 | (CH₃)₂C | H | H | H | H | NO₂ | H | OSO₂CH₃ | 178-180 |
| 49 | CH₂ | H | H | H | H | NO₂ | H | OSO₂phenyl | 157-158 |
| 50 | CH₂ | CH₃ | CH₃ | H | H | NO₂ | H | OSO₂CH₃ | 96-98 |
| 51 | CH₂ | CH₃ | SCH₃ | H | H | NO₂ | H | OSO₂CH₃ | 139-140.5 |
| 52 | CH₂ | CH₃ | SCH₃ | CH₃ | CH₃ | NO₂ | H | OSO₂CH₃ | sticky |
| 53 | CH₂ | CH₃ | CH₃ | CH₃ | CH₃ | NO₂ | H | OSO₂CH₃ | 56-61 |
| 54 | CH₂ | H | H | H | H | NO₂ | H | OSO₂C₂H₅ | 103-105 |
| 55 | CH₂ | CH₃ | CH₃ | H | H | NO₂ | H | OSO₂C₂H₅ | 95-96 |
| 56 | CH₂ | H | H | H | H | NO₂ | H | OSO₂iC₃H₇ | 100-101 |
| 57 | CH₂ | CH₃ | CH₃ | H | H | NO₂ | H | OSO₂iC₃H₇ | 98-100 |
| 58 | CH₂ | CH₃ | SCH₃ | H | H | NO₂ | H | OSO₂C₂H₅ | 110-111 |
| 59 | CH₂ | CH₃ | SCH₃ | H | H | NO₂ | H | OSO₂iC₃H₇ | 115-116 |
| 60 | O | CH₃ | H | CH₃ | CH₃ | NO₂ | H | OSO₂CH₃ | |
| 61 | O | C₂H₅ | H | CH₃ | CH₃ | NO₂ | H | OSO₂CH₃ | |
| 62 | CH₂ | CH₃ | CH₃ | CH₃ | H | NO₂ | H | OSO₂CH₃ | 116-119 |
| 63 | CH₂ | CH₃ | CH₃ | CH₃ | H | NO₂ | H | OSO₂C₂H₅ | |

TABLE B

| Cpd | X₁ | X₂ | R₁ | R₂ | R₅ | R₆ | R₇ | m.p. (°C.) |
|-----|----|----|----|----|----|----|----|----|
| 64 | CH₂ | NCH₃ | CH₃ | CH₃ | NO₂ | H | OSO₂CH₃ | 125.5-127.5 |
| 65 | CHCH₃ | NCH₃ | H | H | NO₂ | H | OSO₂CH₃ | 121-123 |
| 66 | CHCH₃ | NCH₃ | CH₃ | H | NO₂ | H | OSO₂CH₃ | 142-144 |
| 67 | C(CH₃)₂ | NCH₃ | H | H | NO₂ | H | OSO₂CH₃ | |
| 68 | C(CH₃)₂ | NCH₃ | CH₃ | H | NO₂ | H | OSO₂CH₃ | |
| 69 | C(CH₃)₂ | NCH₃ | CH₃ | CH₃ | NO₂ | H | OSO₂CH₃ | |
| 70 | C=O | C(CH₃)₂ | CH₃ | CH₃ | NO₂ | H | OSO₂CH₃ | |

Especially good activity has been demonstrated by Compound Nos. 28, 50, 53, 54, 55, 62, 104 and 105.

The starting compounds, e.g. the compounds of formula II herein are known or, in cases where they are novel, can be produced by methods analogous to known methods or by methods described herein.

Thus, the enol esters of formula II can be prepared by the reaction of a 3,5-dione of formula III with a benzoyl halide of formula IV (wherein Q is a halogen atom) in the presence of a moderate base such as triethylamine.

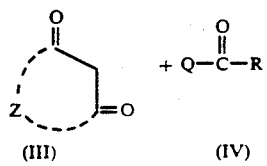

Cycloalkanediones of formula III are known in the art or can be prepared according to procedures that are analogous to known procedures.

In particular, compounds of formula IIIa

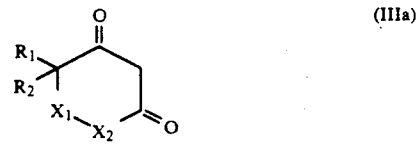

are known in the art e.g. from U.S. Pat. No. 4,728,745; 4,808,720 and EP 40082, EP 90262 and EP 283152 and may be prepared by methods disclosed or referenced therein or analogously to the examples hereinafter.

2H-Pyran-3,5-(4H,6H)-diones of formula IIIa (where $X_1$ is oxygen) can be synthesized by methods such as a) described by Morgan et al., JACS 79:422 (1957), or b) by treating a 2,5-substituted furanidine-3,4-dione (from Korobitsyn et al., Gen. Cheml USSR 27:1859 (1957) with an alkyl diazoacetate, followed by heating in the presence of water.

The 2H-thiopyran-3,5-(4H,6H)-diones and piperidines of formula IIIa (where $X_1$ is sulfur or $NR_{11}$) can be synthesized by reacting a sulfide or sarcosinate of formula V (alk=methyl or ethyl and $X_1=S$ or $NR_{11}$) with sodium methoxide.

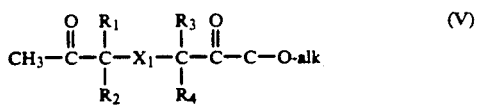

The bicycloalkane diones of formula III can be prepared, for example, by reacting an acetylcycloalkene of formula VI (where m is zero to four) with a substituted diethyl malonate of formula VII to give a compound of formula III where q is one.

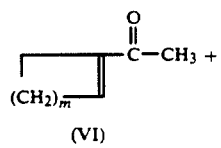

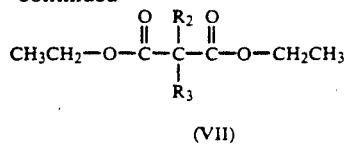

The acyl halides of formula IV can be prepared from the corresponding substituted benzoic acids according to the teaching of *Reagents for Organic Synthesis*, Vol. I. L. F. Fieser and M. Fieser (1967)

INTERMEDIATE COMPOUNDS

The following examples are presented to illustrate representative methods of preparing the intermediate compounds.

EXAMPLE 10

Boron trifluoride etherate (4.8 ml, 39.0 mmol) is added to a solution of 2,2,5,5-tetramethylfuranidine-3,4-dione (15.0 g, 78.0 mmol) in 20 ml of anydrous ether. Ethyl diazoacetate (12.3 ml, 117.0 mmol) in 20 ml of ethyl ether is added at a rate such that nitrogen evolution does not become vigorous. The mixture is stirred at RT for 12 hours and is then quenched with water. The mixture is diluted with ether and washed with brine, then extracted with 5% $K_2CO_3$. The $K_2CO_3$ solution is washed with ether and neutralized with conc. HCl. The product is extracted with ether, dried and evaporated to give 4-carbethoxy-2,2,6,6-tetramethyl-2H-pyran-3,5-(4H,6H) dione, a pink oil.

The above trione (5.11 g, 21.1 mmol) is dissolved in 25 ml of dimethyl sulfoxide, and water is added (0.8 ml. 42.2 mmol). The mixture is heated at 120° for 1 hour, or until gas evolution has ended. The reaction mixture is diluted with ether and washed with sat. NaCl. The solvent is removed and the crude product triturated with ether/hexane to give 2,2,6,6-tetramethyl-2H-pyran-3,5-(4H,6H)-dione, as white crystals.

EXAMPLE 11

To a solution of 4-hydroxy-3-methoxy-2-nitrobenzaldehyde (10.0 g, 50.7 mmol) in 200 ml of methylene chloride and containing triethylamine (10.60 ml, 1.5 eq.) at 0° is added methanesulfonyl chloride (4.32 ml, 6.39 g, 1.1 eq.) over a period of 5–10 min. The mixture is stirred for an additional 10 min., and is then washed with ice water, with dilute HCl, with sat. NaHCO₃ and with brine. The layers are separated and the organic layer is dried and evaporated to give 3-methoxy-4-methylsulfonyloxy-4-nitrobenzaldehyde.

The above aldehyde (13.25 g) is suspended in acetone and cooled to 0°. Jones reagent is added dropwise over approx. 15 min. until the solution is slightly orange, indicating an excess of the reagent. The reaction is stirred for approx. 1 hr., after which it is diluted with water and extracted with ethylacetate to give 3-methoxy-4-methylsulfonyloxy-2-nitrobenzoic acid.

EXAMPLE 12

3-Methoxy-4-methylsulfonyloxy-2-nitrobenzoic acid(5.13g,17.6mmol) is heated under reflux with thionyl chloride for 2 hr., after which excess thionyl chloride is removed under vacuum. The resulting acid chloride residue is added to 2,2,6,6-tetramethyl-2H-pyran-3,5-(4H-6H)-dione (3.00 g, 17.6 mmol) and dissolved in 50 ml of methylene chloride, with cooling to 5°, followed by dropwise addition of triethylamine (3.19 ml, 1.3 eq.). The mixture is stirred at RT for 2 hr. and then poured into water. The organic layer is washed with brine, dried and evaporated to give 2,2,6,6-tetramethyl-5-(3-methoxy-4-methylsulfonyloxy -2-nitrobenzoyloxy)-3,6-dihydro-2H-pyran-3-one.

EXAMPLE 13

To a solution of 2-chloro-4-hydroxybenzoic acid (3 45 g, 20 mmol) and sodium hydroxide (2.40 g, 60.0 mmol) in 30 ml of water is added, dropwise at 0°, methanesulfonyl chloride (2.57 ml, 3.80 g, 33.0 mmol). After addition is complete, the reaction mixture is stirred at RT for 30 min., after which it is poured into water, acidified with dil. HCl and extracted with ether. The combined organic extracts are washed with brine, dried and evaporated to give 2-chloro-4-methylsulfonyloxybenzoic acid.

EXAMPLE 14

To a solution of 5-methylcyclohexane-1,3-dione (1.79 g, 14.0 mmol) in 20 ml of methylene chloride containing triethylamine (2.90 ml, 20.8 mmoles) is added, dropwise at 0°, a solution of 2-chloro-4-methylsulfonyloxybenzoyl chloride, prepared from the corresponding acid (3.50 g, 14.0 mmol) and thionyl chloride, in methylene chloride (10 ml). After the addition is complete, the mixture is stirred for another 30 min. at 0°, after which it is diluted with methylene chloride, washed, dried and evaporated to dryness. The crude enol ester is treated with triethylamine (3.97 ml, 2 eq.) and acetone cyanohydrin (0.4 ml) in 25 ml of acetonitrile. After stirring overnight at RT, the reaction mixture is concentrated and poured into water. The combined organic extracts are washed with dilute HCl and with brine, dried and evaporated to dryness. The crude product is crystallized from ether to give 2-(2-chloro-4-methylsulfonyloxybenzoyl)-5-methyl-cyclohexane-1,3-dione.

EXAMPLE 15

Sodium metal (2.31 g, 101.0 mmol) is dissolved in 50 ml of ethanol, and diethyl methylmalonate (17.6 g, 101.0 mmol) is added, after which the mixture is stirred for approx. 30 min. under reflux. 1-Acetyl-1-cyclohexane (12.50 g, 101.0 mmol) is added and the mixture is stirred under reflux overnight. Potassium hydroxide (12.47 g, 222.2 mmol) dissolved in 40 ml of water is added and the mixture is heated under reflux for 4 hr. The ethanol is removed by rotary evaporation, and the residue is dissolved in water and washed with ether. The aqueous layer is acidified with conc. HCl and extracted with ether. The combined extracts are dried and the solvent is removed to give 4a,5,6,7,8,8a-hexahydro-4-methyl-naphthalene-1,3-(2H,4H)-dione.

To a mixture of the above dione (8.0 g, 44.4 mmol) and 2-chloro-4-methylsulfonyloxybenzoyl chloride (44.4 mmol) in 50 ml of methylene chloride is added, dropwise, triethylamine (8.04 ml, 1.3 equiv.), and the mixture is stirred at RT for 2 hr. The reaction mixture is diluted with methylene chloride, washed with water and evaporated to give 1-(2-chloro-4-methylsulfonyloxybenzoyloxy)-4a,5,6,7,8,8a-hexahydro-4-methyl-3-(4H)-naphthalenone and 3-(2-chloro-4-methylsulfonyloxybenzoyloxy)-4a-5,6,7,8,8a-hexahydro-4-methyl-1(4H)-naphthalenone.

EXAMPLE 16

Following the procedure of Example 12, the sodium salt of diethyl malonate (161.0 mmol) and 1-acetyl-2-methyl-1-cyclopentene (20.0 g, 161.0 mmol) are reacted together to give 7a-methyl-2,3,7,7a-tetrahydro-1H-indene-4,6(5H)-dione, which is then reacted with 2-chloro-4-methylsulfonyloxybenzoyloxy)-7a-methyl-2,3,7,7a-tetrahydro-1H-inden-6-one and 6-(2-chloro-4-methylsulfonyloxybenzoyloxy)-7a-methyl-2,3,7,7a-tetrahydro-1H-inden-4-one.

EXAMPLE 17

To a solution of 2,4 g of 2,2,4,4-tetramethylcyclohexane-1,3,5-trione in 35 ml of methylene chloride containing 1.4 g of triethylamine is added dropwise a solution of 4-methylsulfonyloxy-2-nitrobenzoylchloride and the mixture is stirred for 2 hrs. The resulting mixture is washed with water, dried over Na$_2$SO$_4$, filtered and the solvent evaporated to yield 4,4,6,6-tetramethyl-1-(4-methylsulfonyloxy-2-nitrobenzoyloxy)-1-cyclohexane-3,5,-dione as an oil.

EXAMPLE 18

A stirred suspension of 2.35 g of 4-methylsulfonyloxy-2-nitrobenzoic acid in 10 ml of thionylchloride is refluxed under N$_2$ for 2 hr. Excess thionylchloride is removed by vacuum distillation and the resulting syrup dried under high vacuum at RT and dissolved in 10 ml of CH$_2$Cl$_2$. This cooled solution is added dropwise to a stirred solution of 1,5,5-trimethyl-4-oxavalerolactam in 15 ml of CH$_2$Cl$_2$ and 2.0 ml of triethylamine under N$_2$. After stirring for 45 mins the mixture is diluted with 25 ml CH$_2$Cl$_2$ washed with water and sat. NaCl, dried over Na$_2$SO$_4$, filtered and evaporated to dryness to yield the starting material of Example 9.

EXAMPLE 19

The lactam of Example 18 may be prepared according to the following reaction scheme.

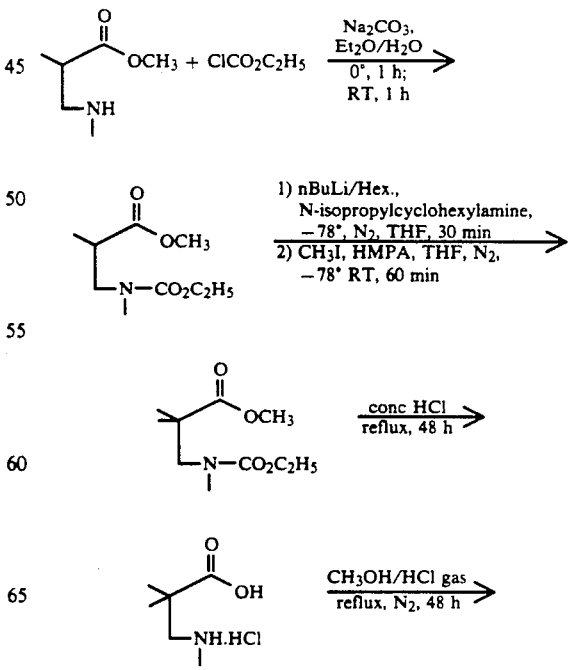

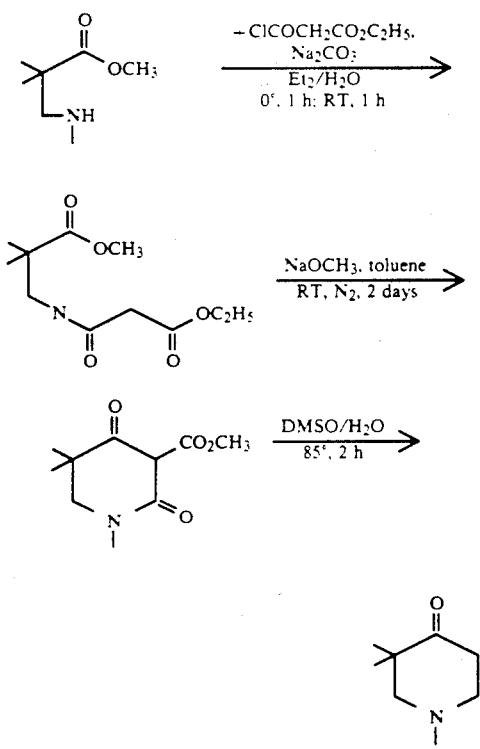

BIOASSAY

EXAMPLE F

Paddy soil in plastic pots (200 cm³) is just flooded and then puddled. Water depth is maintained at 4 cm during testing without water drainage treatment. The field is seeded with barnyard-grass, monchoria, ammania and bulrush. The tubers of Sagittaria trifolia, pygmaea, water nutsedge and water chestnut are buried in the field. Six rice seedlings in a diphyllous stage (breed: Koshihikari, 1 cm plating: 3 rice seedlings, 3 cm plating: 3 rice seedlings) per pot are transplanted. After 10 days from the transplantation, the powder formulated according to Example E is spread over the surface of water. On the next day after the application and on the day after next, water is allowed to leak out at a rate of 3 cm/day. On the 21st day after the application, evaluation is made by observing degree of damage to the plants.

Excellent weed control is achieved with little or no rice crop damage at rates of 125 g/ha or less using e.g. compounds 28, 104 and 105.

EXAMPLE G a) Preemergent

Weeds and crop plants are seeded two per pot and covered with soil. The active ingredient is sprayed onto the surface of the soil at the chosen application rate with a spray volume equivalent to 600 L/Ha (50% acetone, ½% surfactant remainder water). 4 pots per a.i. and species. Evaluation of percentage control takes place at 10 and 28 days post application.

b) Postemergent

Methodology as a) except that spraying takes place at the 2 leaf stage and evaluation of percentage control after 14 and 28 days.

Excellent control of both broadleaf and grassy weeds was obtained at 300 g/ha or less with low damage to corn and rice e.g. with compounds 28, 50, 53, 54 and 55.

What is claimed is:

1. A compound having the formula Ia

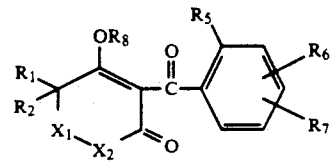

wherein
one of $X_1$, $X_2$ represents $CR_1'R_2'$ and the other represents

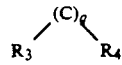

$R_1$, $R_1'$, $R_2$, $R_2'$, $R_3$ and $R_4$ are independently hydrogen, $C_{1-8}$alkyl, $C_{1-8}$alkoxy, $C_{1-8}$alkylthio or $COOR_{16}$ and $R_4$ may additionally represent hydroxy;

$R_5$ is $C_{1-8}$alkyl, optionally substituted with one to six halogen atoms; $C_{1-8}$alkoxy, optionally substituted with one to six halogen atoms; $-(O)_nS(O)_n'R_{12}$; $-NR_{15}SO_2R_{12}$; halogen; cyano; or nitro;

each of $R_6$ and $R_7$ is independently hydrogen or selected from the values of $R_5$; with the proviso that at least one of $R_5$, $R_6$ and $R_7$ is a group $-OSO_2R_{12}$ or $-NR_{15}SO_2R_{12}$;

$R_8$ is hydrogen or a salt forming moiety;

$R_{12}$ is $C_{1-8}$alkyl, optionally substituted with one to six halogen atoms; or phenyl optionally substituted with one to three members selected from $C_{1-8}$alkyl, $C_{1-8}$alkylcarbonyl, $C_{1-8}$alkoxycarbonyl, $C_{1-8}$alkylsulfonyl, $C(O)NR_{13}R_{14}$, $P(O)(OR_{11}'')_2$ and $R_{13}P(O)OR_{11}''$;

$R_{11}$, $R_{11}''$, $R_{13}$, $R_{14}$, $R_{15}$ and $R_{16}$ are independently hydrogen or $C_{1-8}$alkyl;

n is 0 or 1;

n' is 0, 1 or 2;

q is 0 or 1.

2. A compound according to claim 1 wherein $X_1$ is $CR_1'R_2'$; $X_2$ is

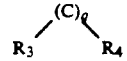

each of $R_1$, $R_1'$, $R_2$, $R_2'$, $R_3$ and $R_4$ is independently hydrogen, $C_{1-8}$alkyl or $COOR_{16}$;

$R_5$ is $C_{1-8}$alkyl, optionally substituted with one to six halogen atoms; $C_{1-8}$alkoxy; optionally substituted with one to six halogen atoms; $O_nS(O)_n'R_{12}$; $NR_{15}SO_2R_{12}$; halogen; cyano; or nitro;

each of $R_6$ and $R_7$ is independently hydrogen or selected from the values of $R_5$; with the proviso that at least one of $R_5$, $R_6$ and $R_7$ is the group $OSO_2R_{12}$ or $NR_{15}SO_2R_{12}$;

$R_8$ is hydrogen;
$R_{12}$ is $C_{1-8}$alkyl, optionally substituted with one to six halogen atoms;
each of $R_{13}$, $R_{14}$, $R_{15}$ and $R_{16}$ is independently, hydrogen, or $C_{1-8}$alkyl;
n is zero or one;
n' is zero, one or two; and
q is zero or one.

3. A compound according to claim 1 wherein
$X_1$ is $CR_1'R_2'$;
$X_2$ is

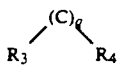

$R_1$, $R_1'$, $R_2$, $R_2'$, $R_3$ and $R_4$ are independently hydrogen, $C_{1-8}$alkyl, $C_{1-8}$alkoxy, $C_{1-8}$alkylthio, or $COOR_{16}$;
$R_5$ is $C_{1-8}$alkyl, optionally substituted with one to six halogen atoms; $C_{1-8}$alkoxy, optionally substituted with one to six halogen atoms; $(O)_nS(O)_n'R_{12}$; $-NR_{15}SO_2R_{12}$; halogen; cyano; or nitro;
each of $R_6$ and $R_7$ is independently hydrogen or selected from the values of $R_5$; with the proviso that at least one of $R_5$, $R_6$ and $R_7$ is a group $-OSO_2R_{12}$ or $-NR_{15}SO_2R_{12}$;
$R_8$ is hydrogen or a salt forming moiety;
$R_{12}$, $R_{15}$ and $R_{16}$, n, n' are as previously defined; and q is 0 or 1.

4. A compound according to claim 1 wherein $R_1$, $R_1'$, $R_2$, $R_2'$, $R_3$ and $R_4$ are independently hydrogen or $C_{1-4}$alkyl;
$R_5$ is $-(O)_nS(O)_n'C_{1-4}$alkyl, halogen, nitro or $C_{1-4}$alkyl optionally substituted by halogen;
$R_6$ is hydrogen, $C_{1-4}$alkyl, $C_{1-4}$alkoxy, $C_{1-3}$alkylsulfonyloxy, bromo or chloro;
$R_7$ is bromo, chloro, $OSO_2C_{1-4}$alkyl, $OSO_2C_{1-4}$haloalkyl, $OSO_2$phenyl or $NR_{15}SO_2 C_{1-4}$alkyl;
$R_{15}$ is hydrogen or $C_{1-4}$alkyl;
q is 1;
n' is 0 or 2.

5. A compound according to claim 4 wherein $R_6$ is in the 3-position and $R_7$ is in the 4-position.

6. A compound according to claim 5 wherein $R_1$, $R_1'$, $R_2$, $R_2'$, $R_3$ and $R_4$ are independently hydrogen or $C_{1-3}$alkyl;
$R_5$ is methyl, $CF_3$, $C_{1-3}$alkylsulfonyl, $C_{1-3}$alkylsulfonyloxy, chloro, bromo or nitro;
$R_6$ is hydrogen, methoxy, methylsulfonyloxy or chloro;
$R_7$ is chloro, $OSO_2$ phenyl or $C_{1-3}$alkylsulfonyloxy; and
$R_{15}$ is hydrogen.

7. A compound according to claim 5 wherein
$R_5$ is nitro;
$R_6$ is hydrogen; and
$R_7$ is $C_{1-2}$alkylsulfonyloxy.

8. A compound according to claim 1 wherein $R_8$ is hydrogen.

9. A compound according to claim 6 wherein $R_8$ is hydrogen.

10. A compound according to claim 1 wherein $R_1$ and $R_2$ are hydrogen
$X_1$ and $X_2$ are $CH_2$;
$R_5$ is nitro or halogen;
$R_6$ is hydrogen;
$R_7$ is in 4-position and represents $C_{1-3}$alkylsulfonyloxy.

11. A compound according to claim 1 which is selected from
2-(4-methylsulfonyloxy-2-nitrobenzoyl)-1,3-cyclohexanedione;
2-(4-methylsulfonyloxy-2-nitrobenzoyl)-4,4,6,6-tetramethyl-1,3-cyclohexanedione; and
2-(4-methylsulfonyloxy-2-nitrobenzoyl)-4,4,6-trimethyl-1,3-cyclohexanedione.

12. An agricultural composition comprising an effective amount of a compound according to claim 1 together with an agriculturally acceptable carrier.

13. A method for the control of weeds or acari which comprises applying to the weed or the acari or their locus an herbicidally or acaricidally effective amount of a compound according to claim 1.

14. A method for selectively controlling weeds in rice which comprises applying to the weeds or their locus a herbicidally effective amount of a compound according to claim 1.